United States Patent
Masuda

(10) Patent No.: US 10,244,952 B2
(45) Date of Patent: Apr. 2, 2019

(54) MEASURING APPARATUS AND MEASURING SYSTEM

(71) Applicant: KYOCERA Corporation, Kyoto (JP)

(72) Inventor: Yuji Masuda, Yasu (JP)

(73) Assignee: KYOCERA Corporation, Kyoto (JP)

( * ) Notice: Subject to any disclaimer, the term of this patent is extended or adjusted under 35 U.S.C. 154(b) by 188 days.

(21) Appl. No.: 15/271,408

(22) Filed: Sep. 21, 2016

(65) Prior Publication Data

US 2017/0086688 A1    Mar. 30, 2017

(30) Foreign Application Priority Data

Sep. 28, 2015 (JP) .................................. 2015-190475
Sep. 28, 2015 (JP) .................................. 2015-190476

(51) Int. Cl.
*A61B 5/024* (2006.01)
*A61B 5/00* (2006.01)
*A61B 5/021* (2006.01)

(52) U.S. Cl.
CPC ...... *A61B 5/02427* (2013.01); *A61B 5/02125* (2013.01); *A61B 5/02438* (2013.01); *A61B 5/6824* (2013.01); *A61B 5/6831* (2013.01); *A61B 2562/043* (2013.01)

(58) Field of Classification Search
None
See application file for complete search history.

(56) References Cited

U.S. PATENT DOCUMENTS

| | | | |
|---|---|---|---|
| 5,309,916 A | 5/1994 | Hatschek | |
| 6,953,435 B2* | 10/2005 | Kondo | A61B 5/021 600/301 |
| 10,085,656 B2 | 10/2018 | Sato | |
| 2014/0051941 A1* | 2/2014 | Messerschmidt | A61B 5/6898 600/301 |
| 2014/0343383 A1 | 11/2014 | Sato | |
| 2017/0095171 A1* | 4/2017 | Park | A61B 5/0022 |

FOREIGN PATENT DOCUMENTS

| | | |
|---|---|---|
| JP | H04-250135 A | 9/1992 |
| JP | 2005-329122 A | 12/2005 |
| JP | 2013-121420 A | 6/2013 |
| WO | 2015/129843 A1 | 9/2015 |

\* cited by examiner

*Primary Examiner* — Brian T Gedeon
(74) *Attorney, Agent, or Firm* — Studebaker & Brackett PC

(57) ABSTRACT

A measuring apparatus 100 includes a wearing portion 110 to be worn by a subject, and a sensor unit 120a and a sensor unit 120b each supported by the wearing portion 110 and having a light emitting unit and a light receiving unit, wherein the sensor unit 120a and the sensor unit 120b, in acquiring a biological-information of the subject when the wearing portion 110 is worn by the subject, are arranged having a distance of 35 mm or less from each other along a predetermined blood vessel of the subject.

19 Claims, 12 Drawing Sheets

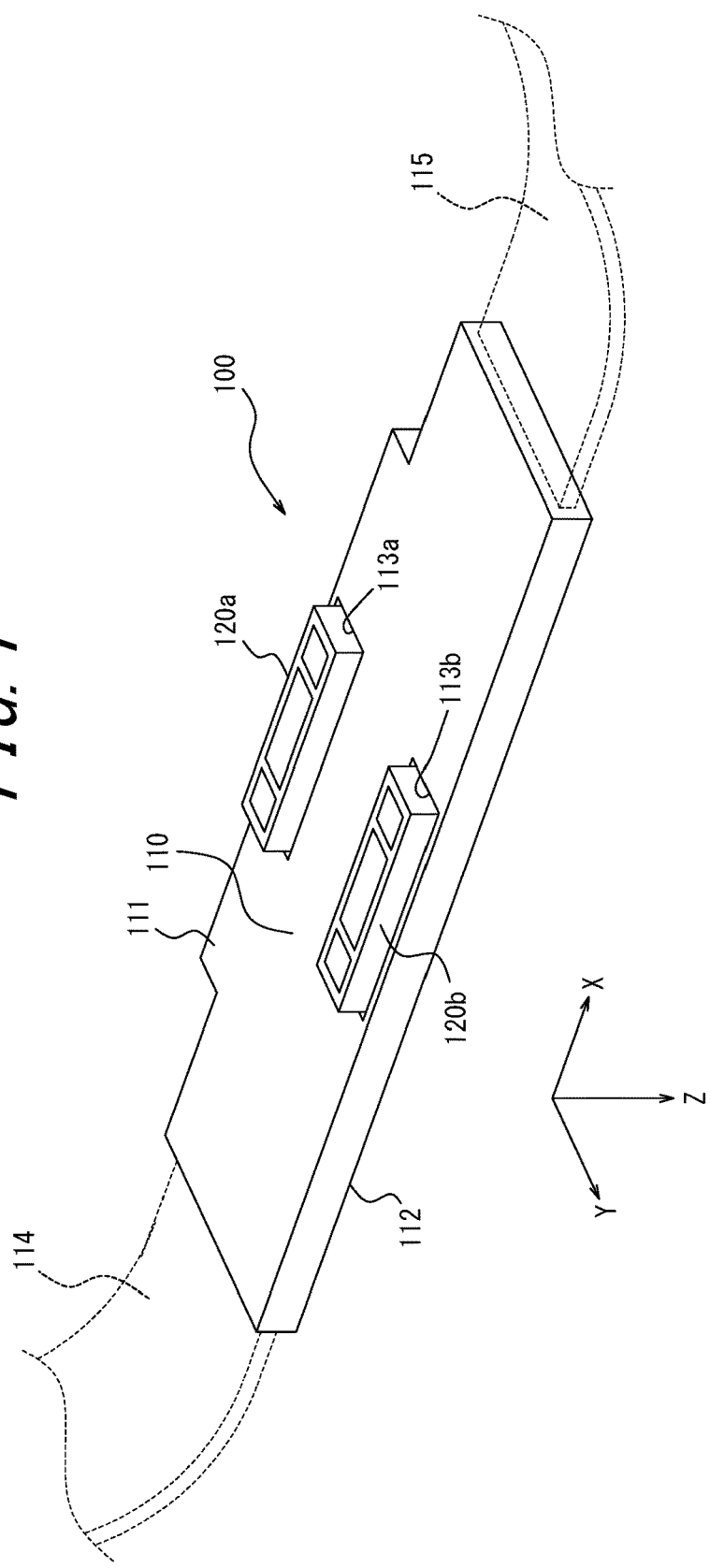

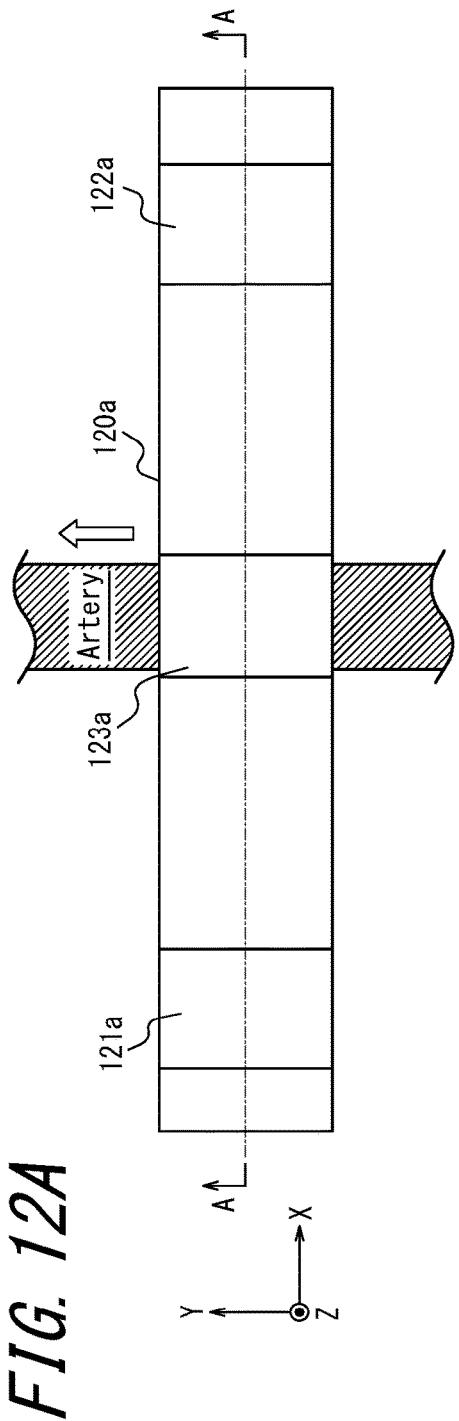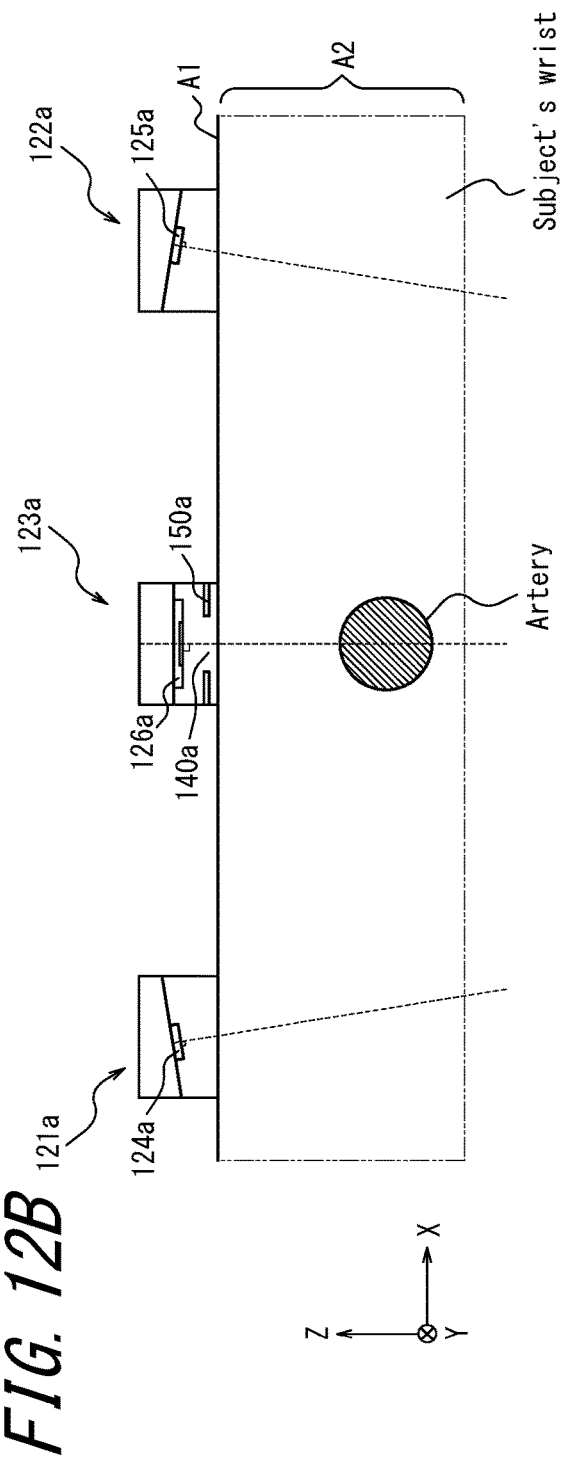

MEASURING APPARATUS AND MEASURING SYSTEM

CROSS REFERENCE TO RELATED APPLICATIONS

This application claims priority to and the benefit of Japanese Patent Applications No. 2015-190475 and No. 2015-190476 both filed on Sep. 28, 2015, the entire contents of which are incorporated herein by reference.

TECHNICAL FIELD

This disclosure relates to a measuring apparatus for measuring biological-information and a measuring system.

BACKGROUND

There has been known a measuring apparatus for measuring biological-information from a test site such as a subject's wrist and the like. For example, a pulse wave velocity measuring apparatus for measuring a pulse wave velocity (Pulse Wave Velocity (PWV)) by placing a pulse wave sensor on a subject's upper arm and knee and detecting a pulse wave at each position has been suggested.

SUMMARY

A measuring apparatus according to one embodiment of the disclosure herein includes a wearing portion, a first sensor unit, and a second sensor unit. The wearing portion is worn by a subject. The first and second sensor units are supported by the wearing portion and respectively include a light emitting unit and a light receiving unit. Also, the first and second sensor units, in acquiring a biological-information of the subject when the wearing portion is worn by the subject, are arranged having a distance of 35 mm or less from each other along a predetermined blood vessel of the subject Also, the measuring apparatus according to one embodiment of the disclosure herein includes the wearing portion to be worn by the subject and the first and second sensor units. The first and second sensor units are supported by the wearing portion and respectively include the light emitting unit and the light receiving unit. The first and the second sensor units, in acquiring a biological-information of the subject when the wearing portion is worn by the subject, are arranged having a predetermined distance from each other along the predetermined blood vessel of the subject. Further, at least one of an optical axis of light emitted from the light emitting unit of the first sensor unit and an optical axis of light entering the light receiving unit of the first sensor unit is inclined to the second sensor unit.

BRIEF DESCRIPTION OF THE DRAWINGS

In the accompanying drawings:

FIG. 1 is a perspective view illustrating appearance of a measuring apparatus according to one embodiment;

FIG. 12A is a schematic diagram illustrating an arrangement of the sensor units of the measuring apparatus according to a sixth embodiment;

FIG. 12B is a schematic diagram illustrating the arrangement of the sensor units of the measuring apparatus according to the sixth embodiment.

DETAILED DESCRIPTION

Figure 2A:
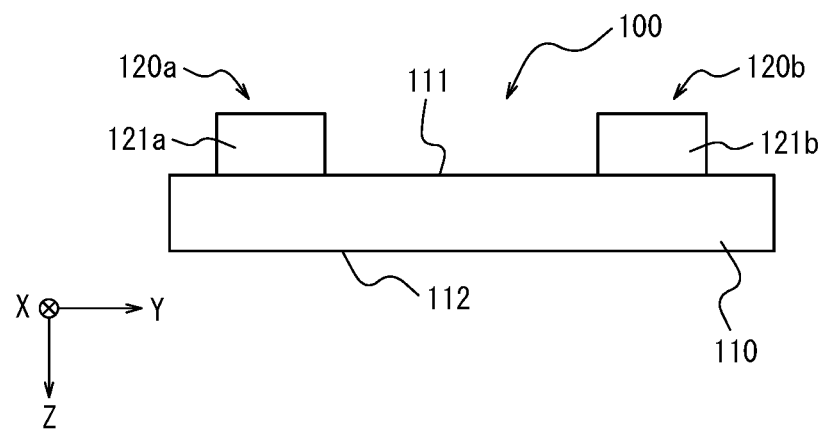
FIG. 2A is a schematic diagram illustrating a portion of the measuring apparatus according to one embodiment and an arrangement therein.

Hereinafter, some embodiments will be described in detail with reference to the accompanying drawings.

FIG. 1 is a schematic cross-sectional view illustrating an outline structure of a measuring apparatus 100 according to one embodiment. As illustrated in FIG. 1, the measuring apparatus 100 includes a wearing portion 110 and sensor units 120*a* and 120*b*. As illustrated in FIG. 1, the wearing portion 110 has a rear surface 111 facing a negative direction of a Z-axis illustrated in the figure and a front surface 112 facing a positive direction of the Z-axis. The measuring apparatus 100 is worn and used with the rear surface 111 of the wearing portion 110 facing a test site of a living body of a subject. Therefore, in a state in which the subject is wearing the wearing portion 110 of the measuring apparatus 100, the subject may view the front surface 112 of the wearing portion 110.

The wearing portion 110 of the measuring apparatus 100 includes openings 113a and 113b on the rear surface 111. The measuring apparatus 100 has a structure in which the sensor unit 120a protrudes from the opening 113a while the sensor unit 120b protrudes from the opening 113b.

Since the wearing portion 110 is used while worn by the subject, the wearing portion 110 preferably includes members such as, for example, belt portions 114 and 115. In FIG. 1, by way of example, the belt portions 114 and 115 to be used to wind around the subject's arm and the like are partially indicated by broken lines. The belt portions 114 and 115 are not limited to a design as illustrated in FIG. 1 but may have any design wearable by the subject. According to one embodiment, the wearing portion 110 may be a belt including the belt portions 114 and 115 to be worn by the subject on the wrist.

The measuring apparatus 100, when being worn by the subject, measures biological-information of the subject. The biological-information measured by the measuring apparatus 100 may be any biological-information measurable by the sensor units 120a and 120b. Hereinafter, by way of example, the measuring apparatus 100 is described to measure PWV by acquiring pulse waves of two sites of the subject.

According to one embodiment, also, the wearing portion 110, including the belt portions 114 and 115, may be a belt in the shape of an elongated strip. The measurement of the biological-information is performed in a state in which, for example, the subject is wearing the wearing portion 110 of the measuring apparatus 100 around the wrist. For example, the subject measures the biological-information by wearing the wearing portion 110 around the wrist in such a manner that the sensor units 120a and 120b contact with the test site. The measuring apparatus 100, on the subject's wrist, measures the PWV of the blood flowing in the ulnar artery or the radial artery.

Figure 2B:
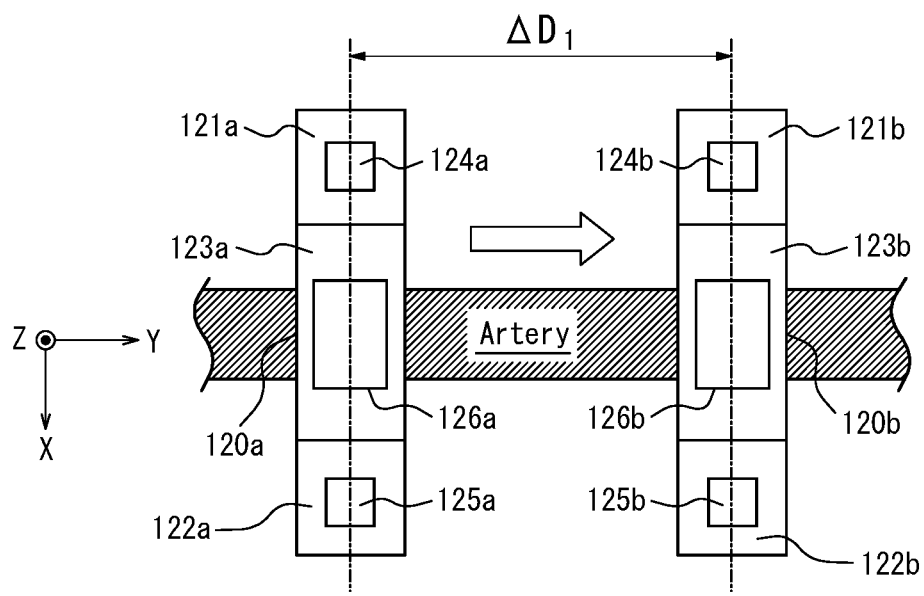
FIG. 2B is a schematic diagram illustrating a portion of the measuring apparatus according to one embodiment and an arrangement therein.

FIG. 2A is a side view schematically illustrating a portion of the measuring apparatus 100 according to one embodiment. FIG. 2A illustrates a lateral face of the measuring apparatus 100 viewed in a positive direction of an X-axis illustrated in FIG. 1. FIG. 2B is a schematic diagram illustrating an arrangement of the sensor units 120a and 120b of the measuring apparatus 100 according to one embodiment. FIG. 2B illustrates the sensor units 120a and 120b of the measuring apparatus 100 viewed in a negative direction of a Z-axis illustrated in FIG. 1. Note that an XYZ coordinate system illustrated in FIGS. 2A and 2B is the same as that in FIG. 1, and the same applies to the other figures.

As illustrated in FIG. 2A, the sensor units 120a and 120b are supported by the wearing portion 110. The measuring apparatus 100 has a structure in which the sensor units 120a and 120b protrude in the negative direction of the Z-axis from the rear surface 111 of the wearing portion 110.

The sensor units 120a and 120b include biosensors for acquiring the biological-information of the subject. The sensor units 120a and 120b measure the biological-information of the subject while being in contact with the test sites of the subject.

As described later, the sensor unit 120a and the sensor unit 120b, in acquiring the biological-information of the subject when the wearing portion 110 is worn by the subject, are arranged along a predetermined blood vessel of the subject. At this time, the sensor unit 120a and the sensor unit 120b are arranged having a distance ΔD1 of 35 mm or less from each other. Also, each sensor unit, as illustrated in FIG. 2B, is arranged vertically to the artery (in an X-axis direction) in which the blood flows in a positive direction of the Y-axis. The sensor units 120a and 120b respectively acquire the pulse waves of different test sites by using an optical method. Here, the pulse wave is a waveform acquired from the body surface representing a chronological change in a volume of the blood vessel caused by inflow of blood, and one of the biological-information. In one embodiment, the sensor units 120a and 120b acquire the pulse wave as the biological-information in an optical manner. Also, based on the pulse wave acquired, a controller of the measuring apparatus 100 calculates the PWV. Note that although in FIG. 2B the sensor unit 120a is arranged on an upstream side of the artery while the sensor unit 120b is arranged on a downstream side, the arrangement thereof is not limited thereto but the sensor units may be interchanged with each other.

As illustrated in FIG. 2B, the sensor unit 120a includes two light emitting units 121a and 122a and a light receiving unit 123a. Similarly, the sensor unit 120b includes two light emitting units 121b and 122b and a light receiving unit 123b. As illustrated in FIG. 2B, the sensor units 120a and 120b are arranged having a predetermined distance from each other along the X-axis. In the sensor unit 120a, the light emitting unit 121a, the light receiving unit 123a, and the light emitting unit 122a are arranged in the mentioned order in the positive direction of the X-axis intersecting the artery. In the sensor unit 120b, similarly, the light emitting unit 121b, the light receiving unit 123b, and the light emitting unit 122b are arranged in the mentioned order in the positive direction of the X-axis intersecting the artery. That is, the light emitting units are arranged on both sides of a corresponding light receiving unit having a predetermined distance from each other along a direction vertical to the predetermined blood vessel of the subject (in the X-axis direction).

As illustrated in FIGS. 2A and 2B, also, the light emitting units 121a, 122a, 121b, and 122b include light emitting elements 124a, 125a, 124b, and 125b, respectively, and the light receiving units 123a and 123b include light receiving elements 126a and 126b, respectively. The light emitted from each light emitting element is transmitted to outside of the light emitting unit and travels through the living body from the subject site. At this time, the light scattered inside the living body is detected by each light receiving element. The pulse wave is acquired in accordance with the intensity of the scattered light detected. The light emitting element is an element such as, for example, LED (Light Emitting Diode), LE (Laser Diode), SLD (Superluminescent Diode), and the like. Also, as the light receiving element, a photodetector element such as, for example, PD (Photodiode), PT (Phototransistor), and the like are applicable. Note that in FIG. 2B each light emitting unit includes one light emitting element and each light receiving unit includes one light receiving element, this is not restrictive; the number of light emitting elements included in the light emitting unit and the number of light receiving elements included in the light receiving unit may be more than one.

Although in the above structure each sensor unit includes two light emitting units and one light receiving unit, according to one embodiment each sensor unit having one light emitting unit and two light receiving units may also conduct the measurement. Or, each sensor unit including one light emitting unit and one light receiving unit may also conduct the measurement. Hereinafter, the structure having two light emitting units and one light receiving unit will be described.

The light emitting units 121a, 122a, 121b, and 122b emit any one of, for example, green light (a wavelength: 500 to 550 nm), red light (the wavelength: 630 to 780 nm), and near-infrared light (the wavelength: 800 to 1600 nm). Since light of a long wavelength, as compared with light of a short wavelength, does not become attenuated before reaching a deeper portion of the body, the measurement of the biological-information by using the light emitting element for emitting the near-infrared light improves measurement accuracy.

Figure 3A:
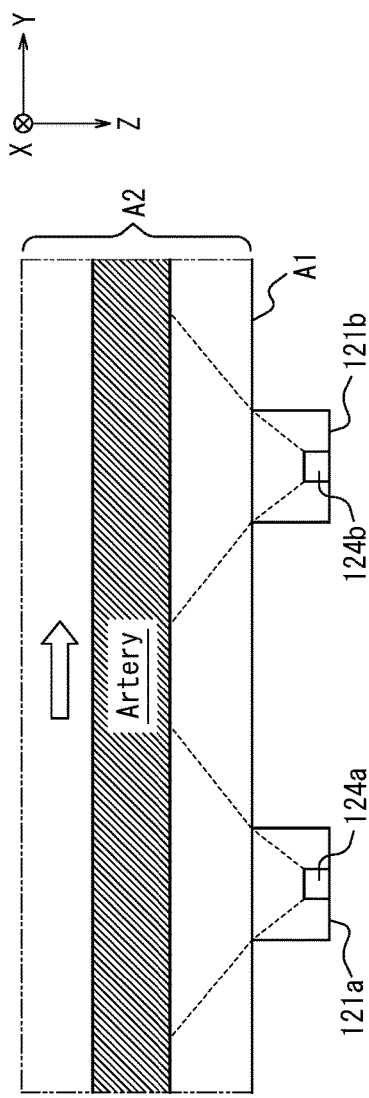
FIG. 3A is a schematic diagram illustrating a portion of the measuring apparatus according to one embodiment and an arrangement therein.
Figure 3B:
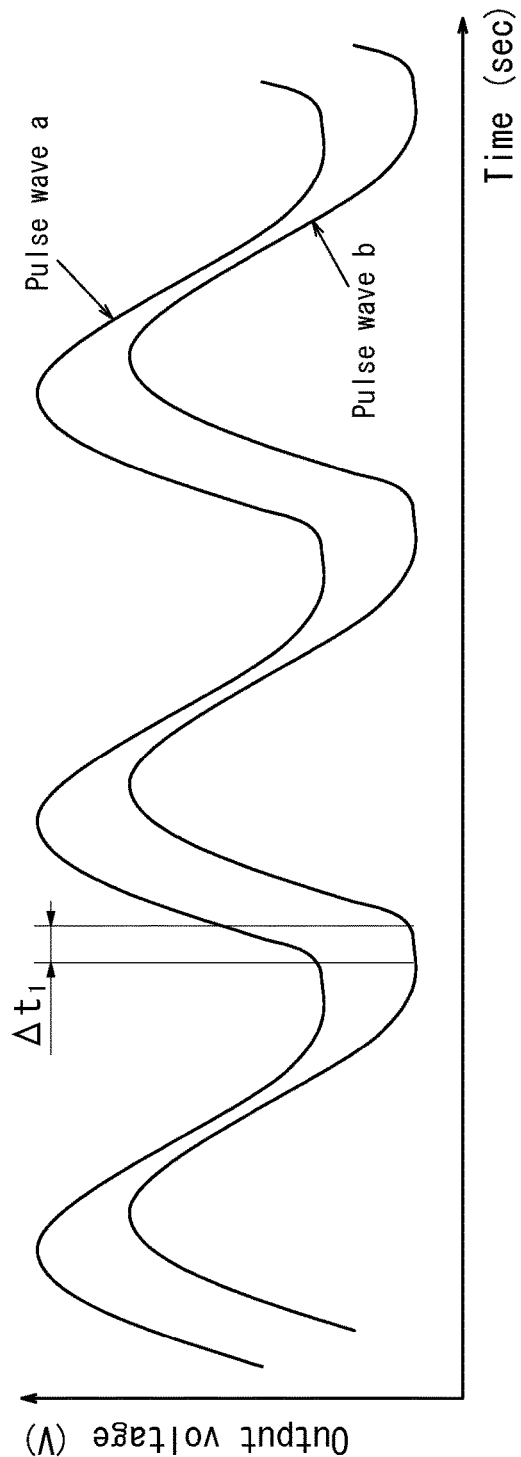
FIG. 3B is a schematic diagram illustrating chronological changes in output voltages output from two light receiving elements.

Based on two pulse waves acquired, a principle of the measurement of the PWV between positions very close to each other on the wrist will be described with reference to FIGS. 3A and 3B. FIG. 3A is a schematic diagram illustrating an ideal condition in which the artery linearly runs between the two sensor units 120a and 120b and keeps the same distance from a skin A1 in an inner living body A2. FIG. 3B is a schematic diagram illustrating, in a state as illustrated in FIG. 3A, a chronological change in an output voltage output from the light receiving element 126a included in the light receiving unit 123a of the sensor unit 120a and the light receiving element 126b included in the light receiving unit 123b of the sensor unit 120b. FIG. 3A especially illustrates, among the light emitting units and the light receiving units of the sensor units 120a and 120b, the light emitting unit 121a of the sensor unit 120a and the light emitting unit 121b of the sensor unit 120b alone. The light emitting units 121a and 121b include the light emitting elements 124a and 124b, respectively, therein. Note that in one embodiment each light emitting element is assumed to be the LED, and each light receiving element is assumed to be the PD.

As illustrated in FIG. 3A, the light emitting units 121a and 121b, in measuring the biological-information, contact with the skin A1 on a surface of the wrist indicated by a solid line. The light emitted from the light emitting elements 124a and 124b enter the inner living body A2 from the skin A1 while largely spreading in an isotropic manner and reaches the artery of a measuring subject of the pulse wave. In the artery, the blood flows from the left to the right (in the positive direction of the Y-axis), and thus the pulse wave is transmitted in the same direction. At this time, the light emitted from the light emitting elements 124a and 124b is scattered upon reaching the artery, and the intensity of the scattered light changes in accordance with a chronological change in a volume of the blood vessel. The light receiving elements 126a and 126b included in the light receiving units 123a and 123b, respectively, detect the scattered light and output the voltage, and thus the pulse wave is acquired. The light receiving units 123a and 123b, in FIG. 3A, are disposed at positions the same as the light emitting units 121a and 121b in the Y-axis and Z-axis directions and different therefrom in the X-axis direction.

FIG. 3B illustrates waveforms of the pulse wave acquired in the ideal condition as illustrated in FIG. 3A. A pulse wave a represents the chronological change in the voltage output from the light receiving element 126a of the sensor unit 120a having the light emitting unit 121a. A pulse wave b represents the chronological change in the voltage output from the light receiving element 126b of the sensor unit 120b having the light emitting unit 121b. FIG. 3B vertically arranges and compares these waveforms.

The sensor unit 120a is arranged on the upstream side of the artery while the sensor unit 120b is arranged on the downstream side of the artery. Therefore, rising of a peak of the pulse wave a occurs earlier than rising of a peak of the pulse wave b by $\Delta t1$. The PWV (m/sec) is acquired by dividing the distance $\Delta D1$ between the sensor unit 120a and the sensor unit 120b by the $\Delta t1$. As described above, assuming the ideal condition in which the artery runs linearly, the pulse wave a and the pulse wave b have the same waveform and a fixed phase difference at any position.

Figure 4:
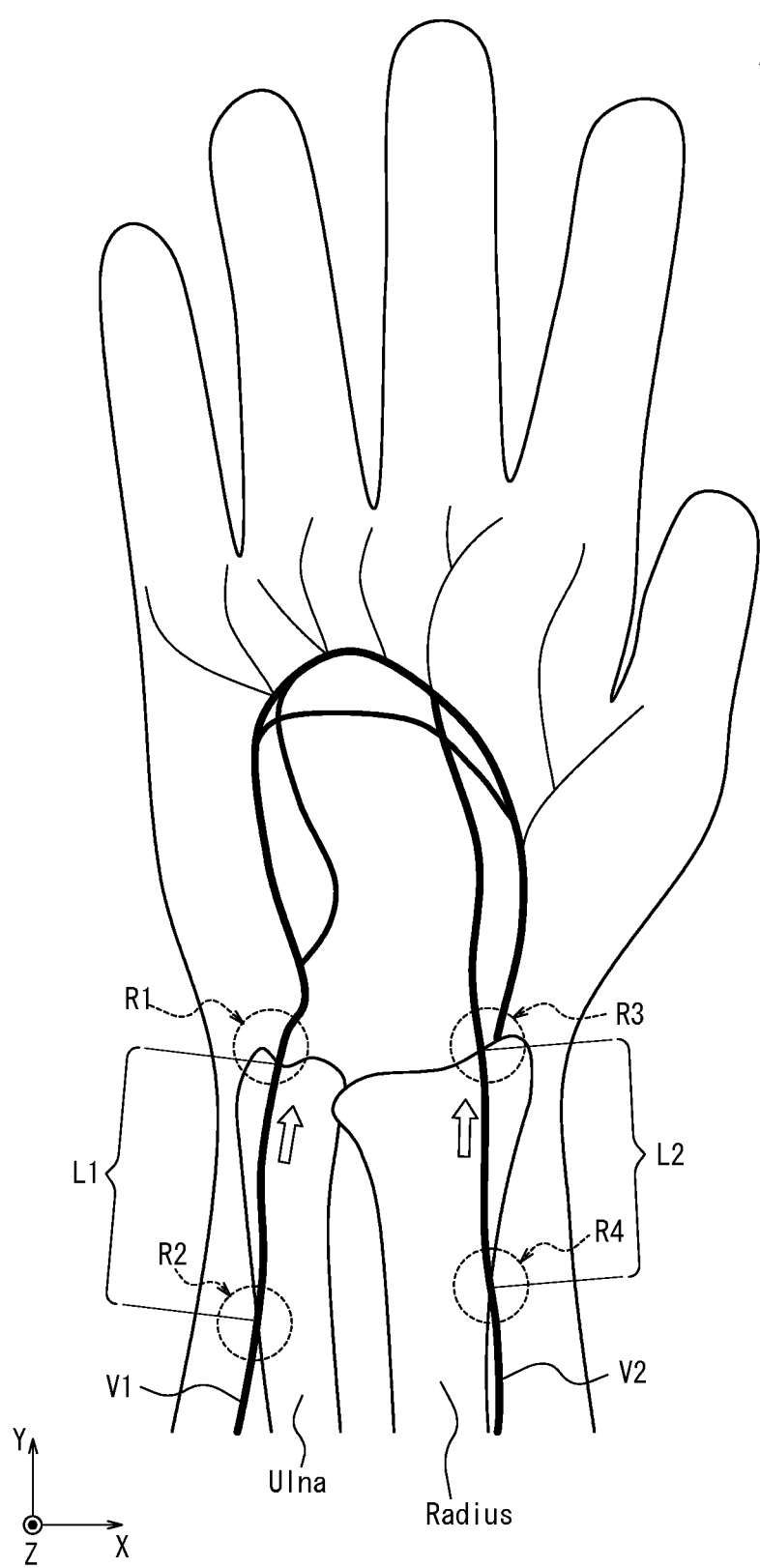
FIG. 4 is a schematic diagram illustrating typical blood flow near a subject's wrist.

However, an actual blood vessel is not in the ideal condition as illustrated in FIG. 3A. The following is a description on the assumption that the biological-information is measured from the actual blood vessel. First, a condition of the actual blood vessel will be described with reference to FIG. 4. FIG. 4 is a diagram schematically illustrating main bones and blood vessels near the right wrist of a typical subject seen through from above the palm. In the right wrist of the typical subject, there are two bones: ulna and radius. Further, two arteries, an ulnar artery V1 and a radial artery V2, run along the ulna and the radius, respectively, inside the living body. In these arteries, the blood flows in directions indicated by respective arrows illustrated in FIG. 4.

Here, as illustrated in FIG. 4, in a region R1 having an end of the ulna, the ulnar artery V1 is positioned along the end of the ulna. Also, in a region R2 in which the ulnar artery V1 is not positioned on the ulna, the ulnar artery V1 penetrates inside the living body. Therefore, the ulnar artery V1, in the regions R1 and R2 illustrated in FIG. 4, enters deep inside the living body from a surface of the skin near the wrist. That is, on a downstream side of the ulnar artery V1 viewed from the region R1 and on an upstream side of the ulnar artery V1 viewed from the region R2, a distance from the skin to the ulnar artery V1 is longer. On the other hand, in a region between the regions R1 and R2, the ulnar artery V1 is positioned on the ulna. Accordingly, since the ulnar artery V1 runs between the ulna and the skin, the ulnar artery V1 is positioned in a shallow portion inside the living body. In the region between the regions R1 and R2, the distance from the skin to the ulnar artery V1 is shorter and, also, substantially constant.

As illustrated in FIG. 4, similarly, in a region R3 having an end of the radius, the radial artery V2 is positioned along the end of the radius. Also, in a region R4 in which the radial artery V2 is not positioned on the radius, the radial artery V2 penetrates inside the living body. Therefore, the radial artery V2, in the regions R3 and R4 illustrated in FIG. 4, enters deep inside the living body from the surface of the skin near the wrist. That is, on a downstream side of the radial artery V2 viewed from the region R3 and on an upstream side of the radial artery V2 viewed from the region R4, a distance from the skin to the radial artery V2 is longer. On the other hand, in a region between the regions R3 and R4, the radial artery V2 is positioned on the radius. Accordingly, since the radial artery V2 runs between the radius and the skin, the radial artery V2 is positioned in a shallow portion inside the living body. In the region between the regions R3 and R4, the distance from the skin to the radial artery V2 is shorter and, also, substantially constant.

In measuring the biological-information from the blood vessel, the test site is preferably positioned where a distance from the skin to the blood vessel is short, i.e., where the blood vessel is positioned in a shallow portion of the living body from the surface of the skin. Also, a condition in which the distance between the skin and the blood vessel in the living body does not change as illustrated in FIG. 3A is ideal.

When such a condition is fulfilled, the pulse wave may be measured more accurately. According to one embodiment, therefore, the test site is positioned immediately above the ulnar artery V1 in the region between the regions R1 and R2 illustrated in FIG. 4 or immediately above the radial artery V2 in the region between the regions R3 and R4.

As a result of observation of the waveform of the pulse wave output while the test site is changed to various positions on the wrist, a length L1 and a length L2 of the ulnar artery V1 and the radial artery V2, respectively, immediately below an optimal test site described above were both 35 mm. As a result of the observation, although there is a slight difference in an arrangement of the blood vessel between people, it was found that the lengths L1 and L2 are 35 mm on average. The region R1 having the end of the ulna may be observed from outside as a protrusion (an ulnar protrusion) of the wrist. The region R3 having the end of the radius may be observed from outside as another protrusion (a radius protrusion) of the wrist. An optimal region of the measurement of the pulse wave is a region on the upstream side of the ulnar artery within 35 mm from the ulnar protrusion. An optimal region of the measurement of the pulse wave is a region on the upstream side of the radial artery within 35 mm from the radial protrusion. An optimal region of the measurement of the pulse wave is a region having the blood vessel between the radial or the ulna and the skin.

Figure 5A:
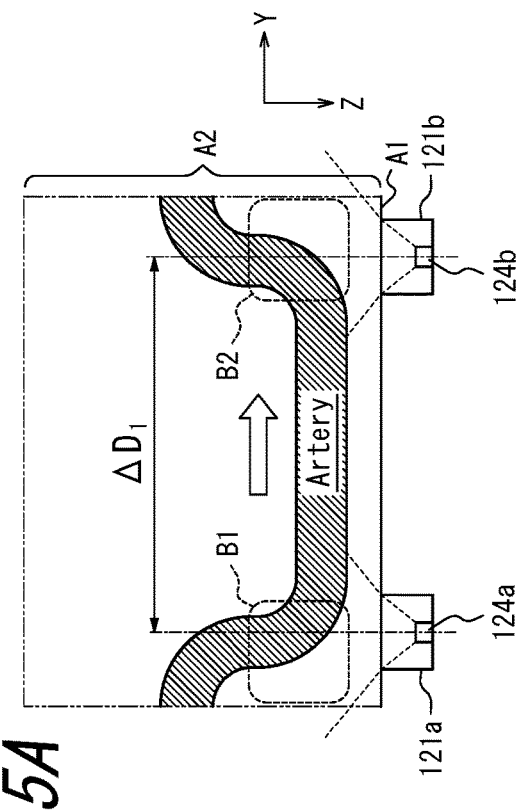
FIG. 5A is a schematic diagram illustrating a portion of the measuring apparatus according to one embodiment and an arrangement therein.
Figure 5B:
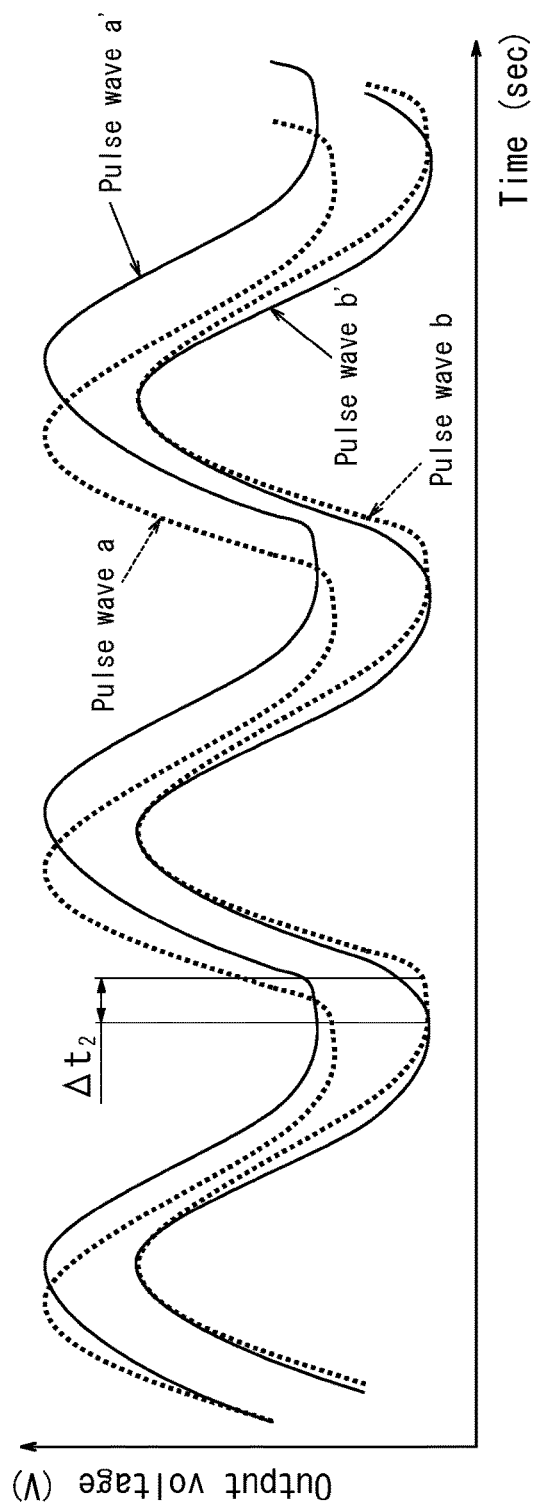
FIG. 5B is a schematic diagram illustrating the chronological changes in the output voltages output from the two light receiving elements.

FIG. 5A is a schematic diagram illustrating a state in which the artery curves near the two sensor units 120a and 120b having a longer distance from the skin A1 (i.e., positioned deeper in the inner living body A2). FIG. 5A illustrates a cross-section of a portion inside the living body and the two sensor units 120a and 120b taken along the Y-axis direction of FIG. 4. As described above, when the subject is a human, a number of subjects typically have the ulnar artery or the radial artery near the wrist having the cross-section as illustrated in FIG. 5A. FIG. 5B is a schematic diagram illustrating the chronological changes in the output voltages output from the light receiving elements 126a and 126b included in the two light receiving units 123a and 123b in the state as illustrated in FIG. 5A. FIG. 5A illustrates, similarly to FIG. 3A, among the light receiving units and the light emitting units, the light emitting unit 121a of the sensor unit 120a and the light emitting unit 121b of the sensor unit 120b alone. The light emitting unit 121a and the light emitting unit 121b include the light emitting elements 124a and 124b, respectively, therein.

Similarly to the condition in FIG. 3A, in the artery, the blood runs in the positive direction of the Y-axis, and thus the pulse wave is transmitted in the same direction. At this time, the light emitted from the light emitting elements 124a and 124b is scattered upon reaching the artery, and the intensity of the scattered light changes in accordance with the chronological change in the volume of the blood vessel. The light receiving elements 126a and 126b included in the light receiving units 123a and 123b, respectively, detect the scattered light and output the voltage, and thus the pulse wave is acquired. The light receiving units 123a and 123b, in FIG. 5A, are disposed at positions the same as the light emitting units 121a and 121b in the Y-axis and Z-axis directions and different therefrom in the X-axis direction.

FIG. 5B illustrates, by using solid lines, waveforms of the pulse waves acquired in the typical condition as illustrated in FIG. 5A. The pulse waves a and b are waveforms of the pulse waves acquired in the ideal condition as illustrated in FIG. 3B indicated by broken lines for a comparison purpose. A pulse wave a' represents the chronological change in the voltage output from the light receiving element 126a of the sensor unit 120a having the light emitting unit 121a. A pulse wave b' represents the chronological change in the voltage output from the light receiving element 126b of the sensor unit 120b having the light emitting unit 121b. FIG. 5B vertically arranges and compares these waveforms.

The light emitted from the light emitting elements 124a and 124b enter from the skin A1 and travels through the inner living body A2 while largely spreading in an isotropic manner. Therefore, the waveform output from each light receiving element includes, in addition to information about the blood vessel immediately below the test site having the sensor units 120a and the 120b arranged thereon, information about the blood vessel on the upstream side and the downstream side of the blood vessel immediately below the test site. That is, in the condition illustrated in FIG. 5A, the output voltage from each light receiving element include information about the pulse wave acquired from a linear portion of the artery and, also, information about the pulse wave acquired from a curved portion of the artery on the upstream side and the downstream side of the linear portion.

In such a condition, first, the pulse wave a' and the pulse wave a are compared with each other. Since the artery has the curved portion on the upstream side of the light emitting element 124a and a longer distance from the skin A1, a distance between the curved portion and the light receiving element 126a becomes also long. The longer the distance to the light receiving element 126a, the weaker the intensity of the scattered light detected. Therefore, the weaker the intensity of the scattered light, the later the rising of a peak of the pulse wave a' occurs as compared to the rising of a peak of the pulse wave a. On the other hand, since the artery on the downstream side of the light emitting element 124a is linear similarly to that of the ideal condition, the falling of the peak of the pulse wave a' synchronizes with the falling of the peak of the pulse wave a. The later the rising of the peak occurs as described above, further a phase of the pulse wave a' shifts in a direction later in time, as compared to a phase of the pulse wave a.

Subsequently, the pulse wave b and the pulse wave b' are compared with each other. Since the artery has a curved portion on the downstream side of the light emitting element 124b and a longer distance from the skin A1, a distance between the curved portion and the light receiving element 126b becomes also long. The longer the distance to the light receiving element 126b, the weaker the intensity of the scattered light detected. Therefore, the weaker the intensity of the scattered light, the earlier the falling of the peak of the pulse wave b' occurs as compared to the falling of the peak of the pulse wave b. On the other hand, since the artery on the upstream side of the light emitting element 124b is linear similarly to that of the ideal condition, the rising of the peak of the pulse wave b' synchronizes with the rising of the peak of the pulse wave b. The earlier the falling of the peak occurs as described above, further a phase of the pulse wave b' shifts in a direction earlier in time, as compared to a phase of the pulse wave b.

Here, the pulse wave a' and the pulse wave b' are compared with each other. The pulse wave a' and the pulse wave b' have phases that, as compared with the waveforms of the respective pulse waves (the pulse wave a and the pulse wave b) acquired in the ideal condition, shift in directions opposite to each other. The phase of the pulse wave a' shifts in the direction later in time, and the phase of the pulse wave b' shifts in the direction earlier in time. Also, similarity between the waveforms of the pulse waves a' and b' is easily lost. Therefore, although in the ideal condition the rising of the peak of the pulse wave a on the upstream side occurs earlier than the rising of the peak of the pulse wave b on the downstream side by the Δt1, in the typical condition the rising of the peak of the pulse wave a' on the upstream side may occur later than the rising of the peak of the pulse wave b' on the downstream side by Δt2. As described above, in actual measuring, when the distance ΔD1 between the two sensor units is not optimally adjusted, at some measuring position of the pulse wave of the artery the peak of the pulse wave b' is detected earlier. Therefore, a waveform indicating, in appearance, the pulse wave flowing back from the right to the left (in the negative direction of the Y-axis) may be acquired.

In the embodiments below, therefore, such a reverse phenomenon of the phase difference between the sensor units 120a and 120b will be eliminated. In each embodiment, a structure different from that described above will be mainly described. For convenience of explanation, also, constituents having the same functions as the constituents described above are denoted by the same reference numerals, and descriptions thereof will be appropriately simplified or omitted. Note that the following embodiments may be applied alone, or in appropriate combinations thereof.

First Embodiment

Figure 6:
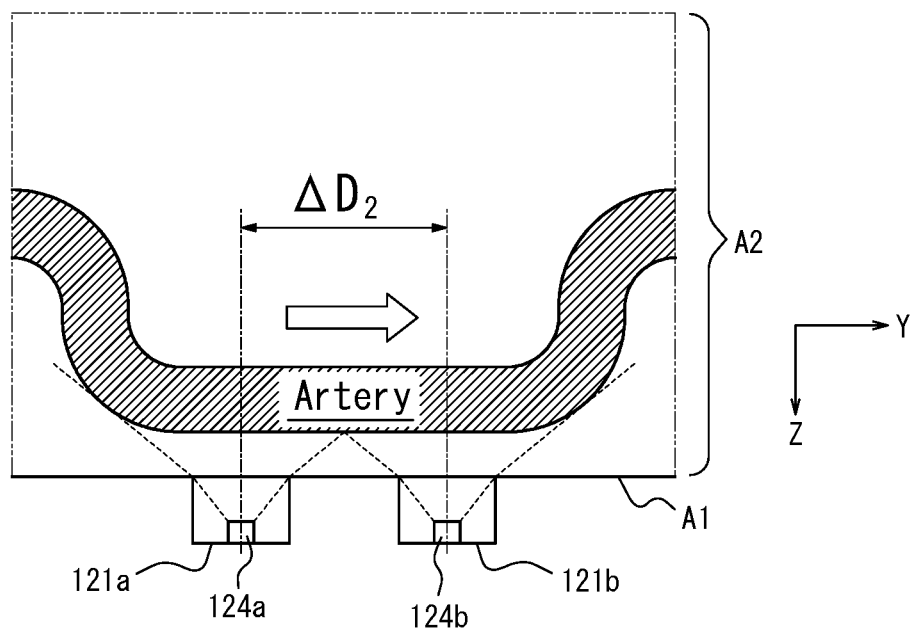
FIG. 6 is a schematic diagram illustrating an arrangement of light emitting units of the measuring apparatus according to one embodiment.

FIG. 6 is a schematic diagram illustrating an arrangement of the sensor units 120a and 120b of the measuring apparatus 100 according to one embodiment. Note that FIG. 6 illustrates, among the constituents of the sensor units 120a and 120b, the light emitting units 121a and 121b and the light emitting elements 124a and 124b alone in a representative manner.

In order to eliminate the reverse phenomenon of the phase difference between the sensor units 120a and 120b, the measuring apparatus 100 according to one embodiment, as illustrated in FIG. 6, optimally adjusts the distance between the sensor unit 120a and the sensor unit 120b. That is, the distance between the sensor unit 120a and the sensor unit 120b is newly defined as ΔD2 smaller than the distance ΔD1 illustrated in FIG. 5A (ΔD2<ΔD1). The sensor units 120a and 120b are disposed at positions such that light emitted from the light emitting elements 124a and 124b is unlikely to reach the curved portion of the artery. Thereby, the phase shift of the pulse wave a' and the pulse wave b' as described with reference to FIG. 5B do not occur, and the ideal pulse wave as described with reference to FIG. 3B may be acquired. When the distance ΔD2 between the sensor units 120a and 120b is increased, the phase difference between the pulse wave a' and the pulse wave b' becomes sufficiently large, allowing the measuring apparatus 100 to measure the pulse wave more accurately. However, when the ΔD2 is increased too much, the sensor units 120a and 120b are disposed immediately above the region (the regions B1 and B2 illustrated in FIG. 5A) where the artery curves and have a longer distance from the skin A1. Accordingly, the intensity of the scattered light detected by the light receiving elements 126a and 126b becomes weak, and the waveform of the pulse wave is unlikely to be output.

Under the condition to be able to detect the waveform of the pulse wave, the distance ΔD2 between the sensor units 120a and 120b has an upper limit. As a result of observation of the waveform of the pulse wave output by changing the test sites to various parts on the wrist, it was found that the upper limit of the distance between the sensor units 120a and 120b is 35 mm. That is, this value may be considered to be similar to the length L1 of the ulnar artery V1 and the length L2 of the radial artery V2 immediately under the optimal test site in FIG. 4. Accordingly, the sensor units 120a and 120b, in acquiring the biological-information of the subject when the wearing portion 110 is worn by the subject, are preferably disposed having the distance of 35 mm or less from each other along the predetermined blood vessel (for example, the ulnar artery or the radial artery near the subject's wrist) of the subject. For example, the light emitting element 124a of the light emitting unit 121a of the sensor unit 120a and the light emitting element 124b of the light emitting unit 121b of the sensor unit 120b are disposed having the distance of 35 mm or less from each other along the predetermined blood vessel of the subject.

On the other hand, since the sensor units 120a and 120b may have a width of approximately 5 mm, a lower limit of the ΔD2 according to one embodiment may be approximately 5 mm (the distance of the light emitting elements of the light emitting units 121a and 121b). However, when the ΔD2 is 5 mm, the phase difference between the output waveforms becomes small, and the output waveforms overlap with each other. Accordingly, under the condition to be able to appropriately measure the PWV, it is reasonable to set the lower limit of the ΔD2 to 10 to 15 mm.

As described above, optimally adjusting the ΔD2 between the lower limit and the upper limit as described above eliminates the reverse phenomenon of the phase difference described above. Thereby, the measuring apparatus 100, while keeping a structure thereof small, may accurately measure the biological-information including the PWV.

Second Embodiment

Figure 7:
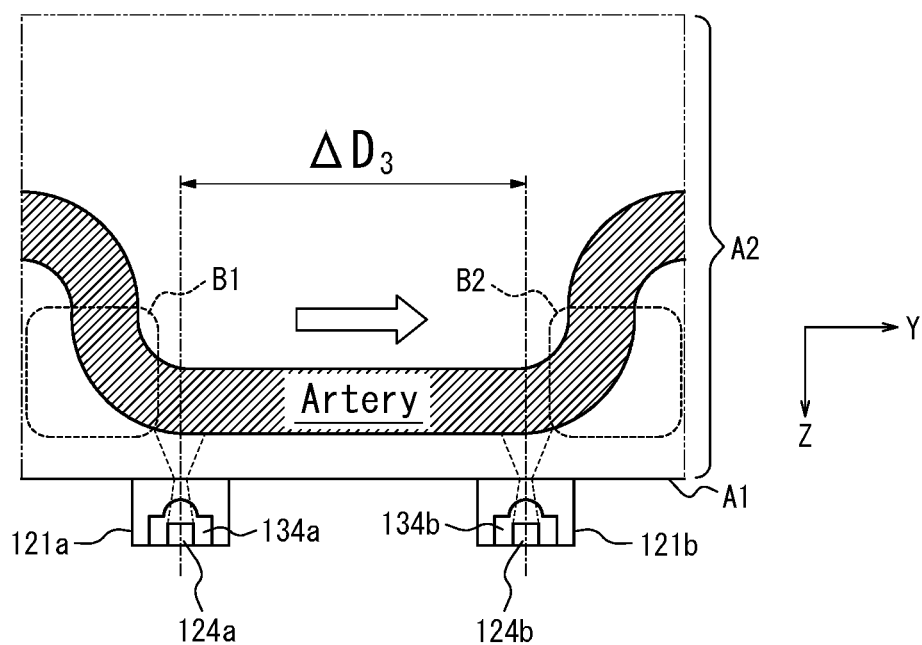
FIG. 7 is a schematic diagram illustrating the arrangement of the light emitting units of the measuring apparatus according to one embodiment.

According to one embodiment, as illustrated in FIG. 7, a lens unit is provided to the light emitting element of the light emitting unit so as to suppress the scattering of the light emitted from each light emitting element. FIG. 7 illustrates, in a representative manner, the light emitting unit 121a of the sensor unit 120a and the light emitting unit 121b of the sensor unit 120b, and the light emitting units 121a and 121b include the light emitting elements 124a and 124b, respectively. According to one embodiment, a lens unit 134a is provided in order to suppress the scattering of the light emitted from the light emitting element 124a, and a lens unit 134b is provided in order to suppress the scattering of the light emitted from the light emitting element 124b. Note that, preferably, the light emitting element included in the light emitting unit 122a of the sensor unit 120a and the light emitting element included in the light emitting unit 122b of the sensor unit 120b are provided with a lens unit in a similar manner.

According to one embodiment, as illustrated in FIG. 7, a distance ΔD3 between the sensor unit 120a and the sensor unit 120b is defined. Similarly to the first embodiment, the ΔD3 is set to be 35 mm or less. That is, the two sensor units 120a and 120b are disposed immediately above the linear portion of the artery. In the artery, the blood flows in the positive direction of the Y-axis illustrated in the figure, and thus the pulse wave is transmitted in the same direction.

At this time, since the light emitted from the light emitting elements 124a and 124b is concentrated by the lens units 134a and 134b, the scattering of the emitted light within the inner living body A2 may be suppressed. A region in which the light entering the inner living body A2 is scattered becomes smaller than a region in which the light is emitted in a wide range without the lens units 134a and 134b. In other words, the light entering the inner living body A2 reaches the linear portion of the artery alone and scattered thereby. According to one embodiment, that is, the output voltage from each light emitting element includes information about the pulse wave acquired from the linear portion of the artery alone and does not include information about the pulse wave acquired from the curved portion on the upstream side and the downstream side of the linear portion.

According to one embodiment, as described above, the information about the pulse wave from the curved portion of the artery which causes the reverse phenomenon of the phase as described above is not included. According to one embodiment, therefore, the measuring apparatus 100 may enhance the accuracy in measuring the pulse wave. According to one embodiment, also, since the lens units 134a and 134b are provided on the light emitting elements 124a and 124b, the light emitted therefrom may be efficiently used. According to one embodiment, that is, the measuring apparatus 100 may prevent the light from entering a direction unrelated to a direction of the artery and conduct efficient measurement.

Third Embodiment

Figure 8A:
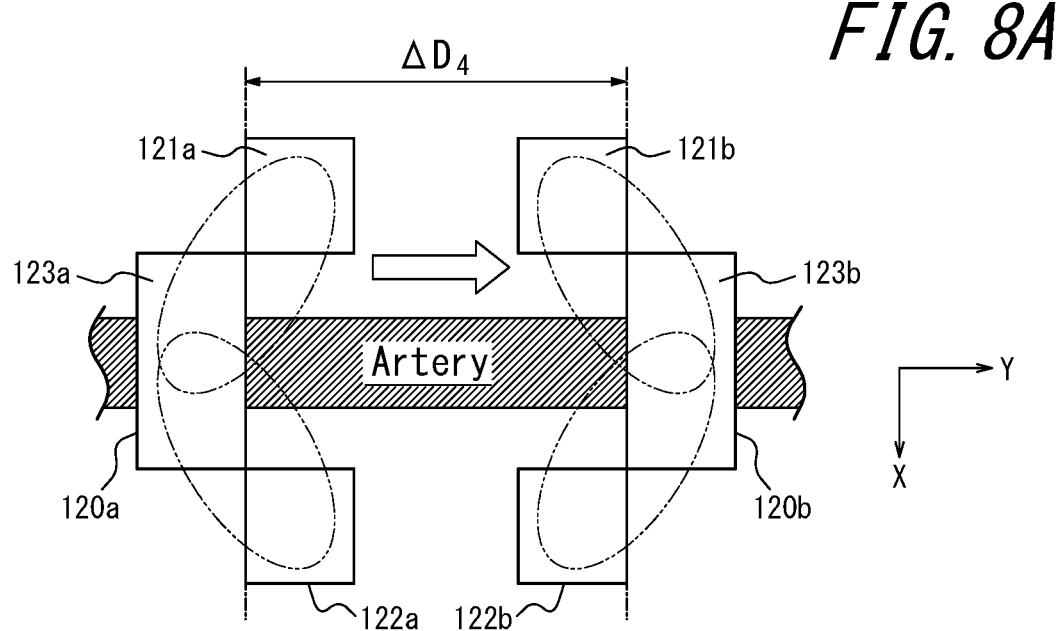
FIG. 8A is a schematic diagram illustrating an arrangement of the sensor units of the measuring apparatus according to a third embodiment and a first embodiment.
Figure 8B:
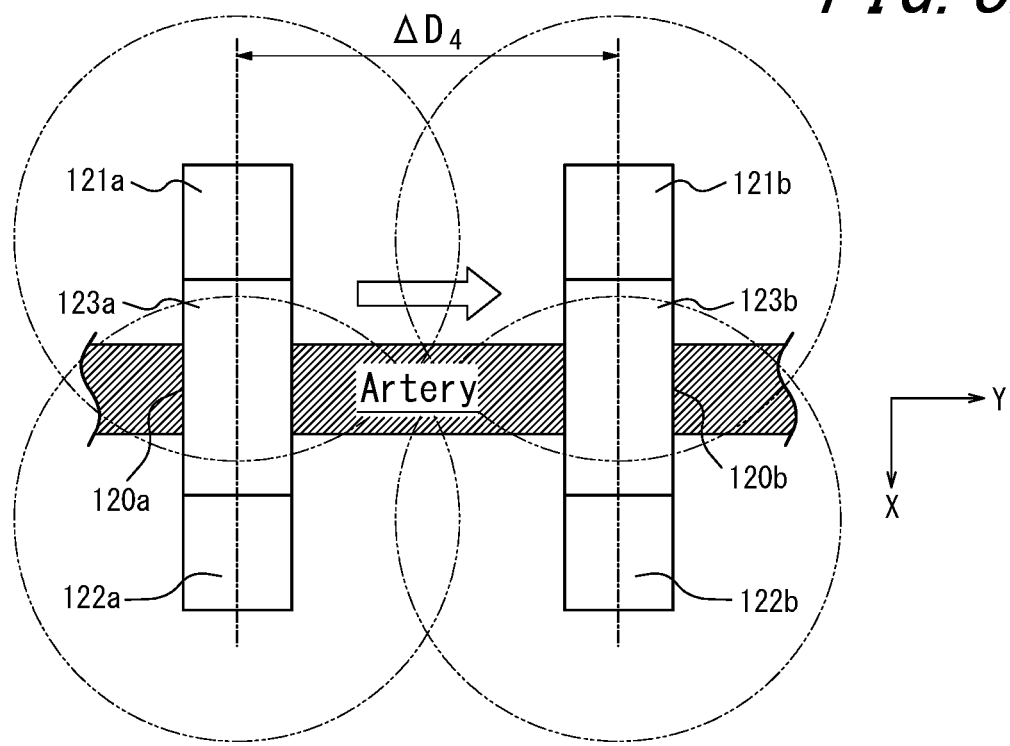
FIG. 8B is a schematic diagram illustrating the arrangement of the sensor units of the measuring apparatus according to the third embodiment and the first embodiment.

FIG. 8A is a schematic diagram illustrating an arrangement of the sensor units 120a and 120b of the measuring apparatus 100 according to one embodiment. FIG. 8B is a diagram illustrating the arrangement of the sensor units 120a and 120b of the measuring apparatus 100 according to the first embodiment once again, for the purpose of a comparison with FIG. 8A. FIG. 8A and FIG. 8B define a distance ΔD4 between the sensor units 120a and 120b. Following the above description, the ΔD4 is set to be 35 mm or less. That is, the two sensor units 120a and 120b are disposed immediately above the linear portion of the artery. As illustrated in FIGS. 8A and 8B, in the artery, the blood flows in the positive direction of the Y-axis, and thus the pulse wave is transmitted in the same direction.

According to one embodiment, as illustrated in FIG. 8A, the distances between the light emitting elements 121a and 122a of the sensor unit 120a and the light emitting elements 121b and 122b of the sensor unit 120b are shorter than the distance between the light receiving unit 123a of the sensor unit 120a and the light receiving unit 123b of the sensor unit 120b. Also, similarly to the second embodiment, each light emitting element is provided with the lens unit so as to suppress the scattering of the light emitted from each light emitting element. In FIG. 8A, the light receiving elements of the light receiving units and the light emitting elements of the light emitting units are omitted. In the first embodiment described above, as illustrated in FIG. 8B, the light emitted from each light emitting element scatters in the isotropic manner. On the other hand, in one embodiment, as illustrated in FIG. 8A, the light emitted from each light emitting element is imparted with directivity. In order to substantialize the directivity, in one embodiment, an optical axis of the light emitted from each light emitting element of the light emitting units 121a and 122a of the sensor unit 120a is inclined to the light receiving unit 123a via the lens unit. Similarly, an optical axis of the light emitted from each light emitting element of the light emitting units 121b and 122b of the sensor unit 120b is inclined to the light receiving unit 123b via the lens unit. According to one embodiment, that is, the light emitted from each light emitting element have different directions between before and after passing through the lens unit. Similarly, the lens unit may be provided to each light receiving element. In this case, the light entering each light receiving element have different directions between before and after passing through the lens unit.

According to one embodiment, information about the blood vessel on the upstream side of the sensor unit 120a and information about the blood vessel on the downstream side of the sensor unit 120b are not included in the scattered light detected by the light receiving elements of the light receiving units 123a and 123b. That is, according to one embodiment, since the information about the pulse wave acquired from the curved portion of the artery is not included in a result of the measurement, the similarity of the waveforms of the pulse waves output from the light receiving elements of the sensor units 120a and 120b is improved, and the reverse of the phase difference may be avoided. According to the third embodiment, also, since the optical axis of the light emitted from each light emitting unit is inclined to a corresponding light receiving unit: the light receiving unit 123a or the light receiving unit 123b, the intensity of the light received by each light receiving element is increased. According to the third embodiment, further, since the optical axis of the light emitted from each light emitting element is included to the light receiving element within the same sensor unit, the light emitted from the light emitting element of one sensor unit is prevented from entering the light receiving element of the other sensor unit. Thereby, the measuring apparatus 100 may accurately measure the pulse wave.

Fourth Embodiment

Figure 9A:
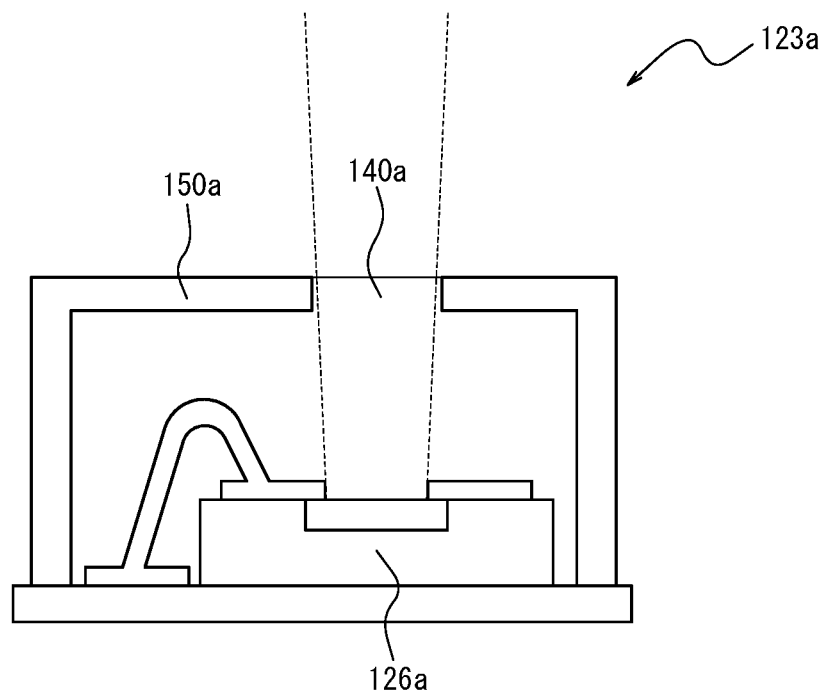
FIG. 9A is a schematic diagram illustrating a package of the light receiving element and an arrangement thereof in the measuring apparatus according to a fourth embodiment.
Figure 9B:
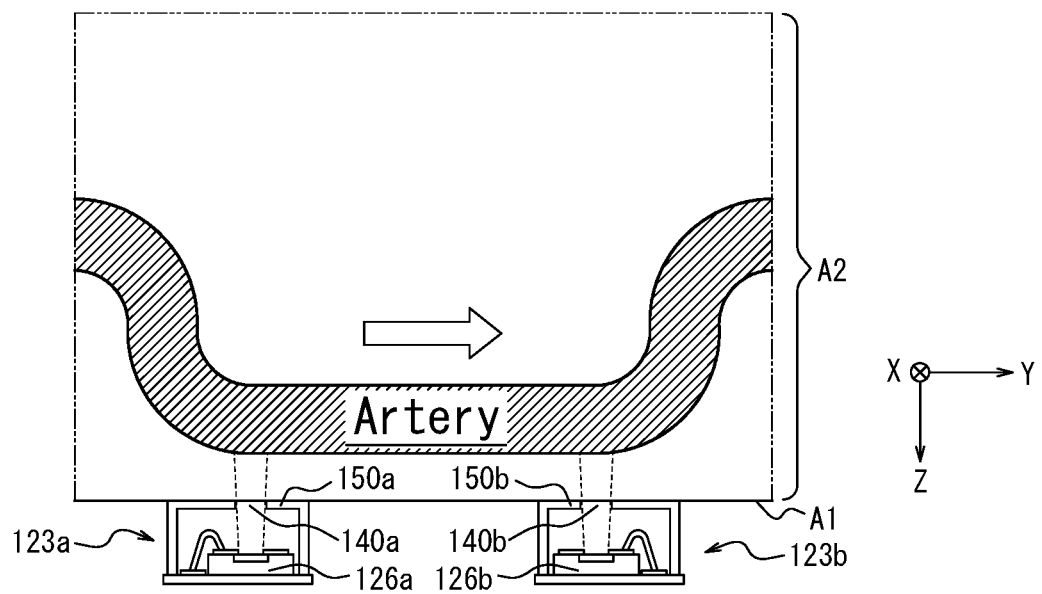
FIG. 9B is a schematic diagram illustrating the package of the light receiving element and the arrangement thereof in the measuring apparatus according to the fourth embodiment.

FIG. 9A is a schematic diagram illustrating a package of the light receiving element 126a of the measuring apparatus 100 according to one embodiment. FIG. 9B is a schematic diagram illustrating a state in which the light receiving units 123a and 123b of the measuring apparatus 100 of one embodiment are disposed along the artery. Note that FIG. 9B omits the two light emitting units of each sensor unit.

As illustrated in FIG. 9A, the light receiving unit 123a includes the light receiving element 126a. In one embodiment, as illustrated in FIG. 9A, the light receiving element 126a is surrounded by a light-shielding plate 150a having an opening 140a with a predetermined diameter. The opening 140a is disposed directly above the light receiving element 126a in such a manner that the light receiving element 126a may detect a portion of the light scattered by the artery. Note that the same configuration as described above is applicable to the light receiving unit 123b.

As illustrated in FIG. 9B, in the artery, the blood flows in the positive direction of the Y-axis, and thus the pulse wave is transmitted in the same direction. In one embodiment, the light shielding plate 150a and a light shielding plate 150b are provided so as to eliminate the scattered light which includes information about an unwanted pulse wave. That is, the light scattered by the curved portion of the artery on the upstream side of the light receiving unit 123a and on the downstream side of the light receiving element 123b is shielded by the light-shielding plates 150a and 150b and prevented from entering the light receiving elements 126a and 126b. Therefore, the light entering from the opening 140a and 140b and detected by the light receiving elements 126a and 126b is limited to the light scattered by the linear portion of the artery.

According to one embodiment, as described above, since the information about the pulse wave acquired from the curved portion of the artery is eliminated by the light-shielding plates 150a and 150b, the similarity of the waveforms of the pulse waves output by the light receiving elements 126a and 126b of the sensor units 120a and 120b is improved, and the reverse of the phase difference may be avoided. Also, since the light receiving elements 123a and 123b are disposed in an extending manner in a direction vertical to the artery (in the X-axis direction), an area of the light receiving unit is enlarged. Thereby, the output voltages output from the light receiving elements 126a and 126b are improved, and a tolerance of disposing positions thereof with respect to the test site is also improved.

Fifth Embodiment

Figure 10A:
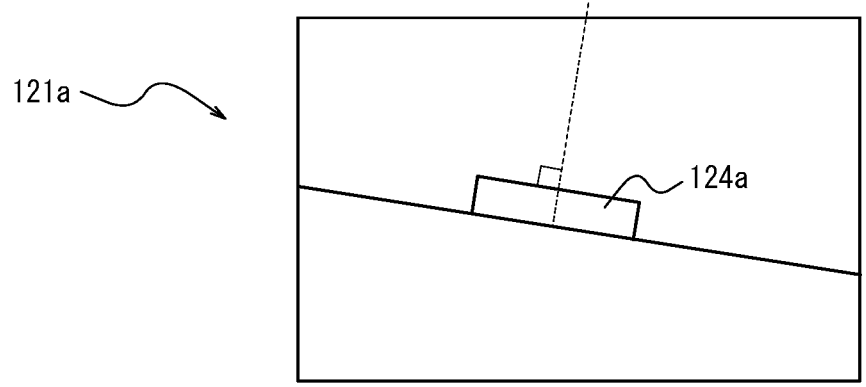
FIG. 10A is a schematic diagram illustrating a structure of the light receiving element and the light emitting element of the measuring apparatus according to a fifth embodiment.
Figure 10B:
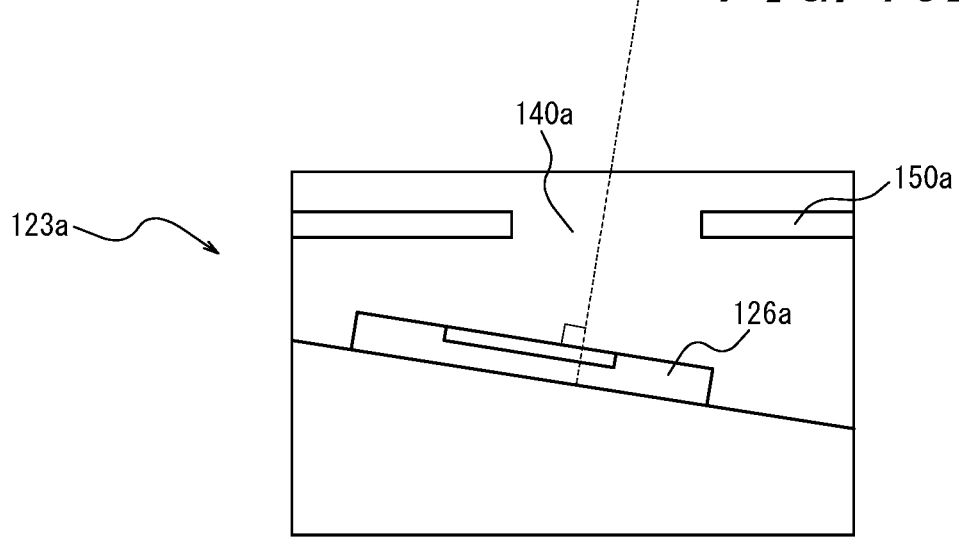
FIG. 10B is a schematic diagram illustrating the structure of the light receiving element and the light emitting element of the measuring apparatus according to the fifth embodiment.

FIG. 10A is a schematic diagram illustrating the light emitting element 124a of the measuring apparatus 100 according to one embodiment. FIG. 10B is a schematic diagram illustrating the light receiving element 126a of the measuring apparatus 100 according to one embodiment.

In one embodiment, at least one of the light emitting element and the light receiving element of the sensor units 120a and 120b is inclined to the other sensor unit. Preferably, three patterns are considered. That is, in a first pattern, the measuring apparatus 100 has a structure in which two light emitting elements and one light receiving element of the sensor unit 120a and two light emitting elements and one light receiving element of the sensor unit 120b are all inclined to the respective opposing sensor units. In a second pattern, the measuring apparatus 100 has a structure in which the two light emitting elements of the sensor unit 120a and the two light emitting elements of the sensor unit 120b alone are inclined to the respective opposing sensor units. In a third pattern, the measuring apparatus 100 has a structure in which one light receiving element of the sensor unit 120a and one light receiving element of the sensor unit 120b alone are inclined to the respective opposing sensor units.

FIG. 10A illustrates, by way of example, a state in which the light emitting element 124a included in the light emitting unit 121a of the sensor unit 120a is inclined to the sensor unit 120b. FIG. 10A is described on the assumption that the sensor unit 120b is disposed on the right side of the light emitting unit 121a. When the light emitting element 124a is inclined, the optical axis of the light emitted from the light emitting element 124a is inclined to the sensor unit 120b. Here, the optical axis is vertical to a light-emitting surface of the light emitting element 124a. Similarly, FIG. 10B illustrates, by way of example, a state in which the light receiving element 126a included in the light receiving unit 123a of the sensor unit 120a is inclined to the sensor unit 120b. Similarly, FIG. 10B is described on the assumption that the sensor unit 120b is disposed on the right side of the light receiving unit 123a. Since the light receiving element 126a is inclined, the optical axis of the light entering the light receiving element 126a is inclined to the sensor unit 120b. Here, the optical axis is vertical to a light entering surface of the light receiving element 126a. Note that, according to one embodiment, similarly to the fourth embodiment, the light receiving element 126a is preferably surrounded by the light-shielding plate 150a having the opening 140a with the predetermined diameter. According to one embodiment, however, unlike the fourth embodiment, the light receiving element 126a is disposed not directly below the opening 140a but slightly closer to the light-shielding plate 150a.

Note that, as described above, it is preferable to essentially incline the light receiving element and the light emitting element included in the light receiving unit or the light emitting unit, without inclining the light receiving unit and the light emitting unit. The light receiving element and the light emitting element, in acquiring the biological-information of the subject when the wearing portion 110 is worn by the subject, are arranged having the predetermined distance from each other along the predetermined blood vessel of the subject. At this time, the light-emitting surface of each light emitting unit from which the light is emitted and the light entering surface of each light receiving unit from which the light enters need to be entirely and sufficiently in contact with the skin on the surface of the wrist serving as the test site of the subject. Therefore, preferably, without inclining each light receiving unit and light emitting unit to the other sensor unit, the light receiving elements and the light emitting elements alone included in the light receiving units or the light emitting units are inclined to the respective opposing sensor units.

Figure 11A:
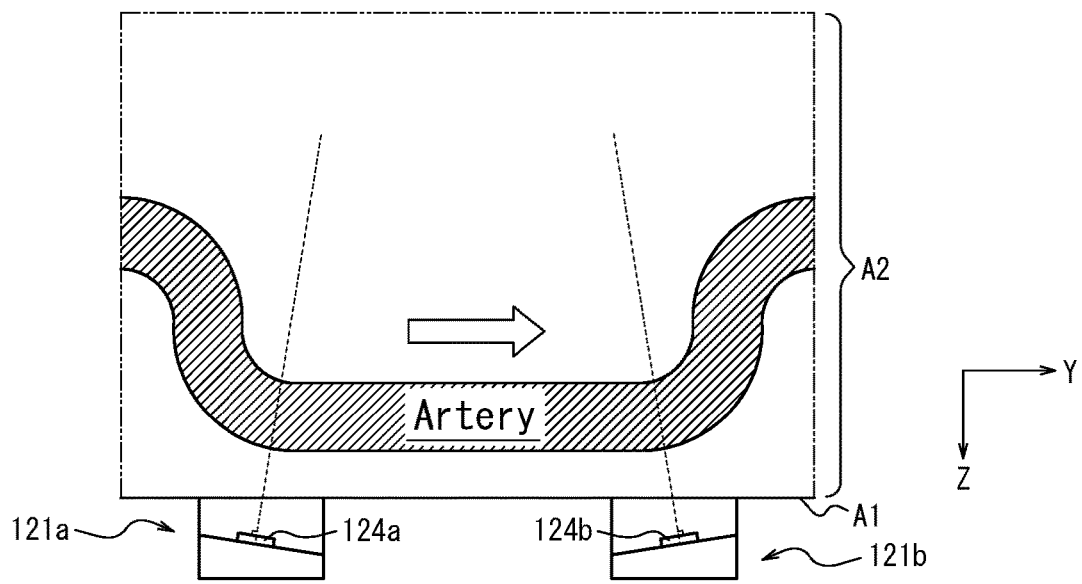
FIG. 11A is a schematic diagram illustrating an arrangement, on a test site, of the light receiving element and the light emitting elements of the measuring apparatus according to the fifth embodiment.
Figure 11B:
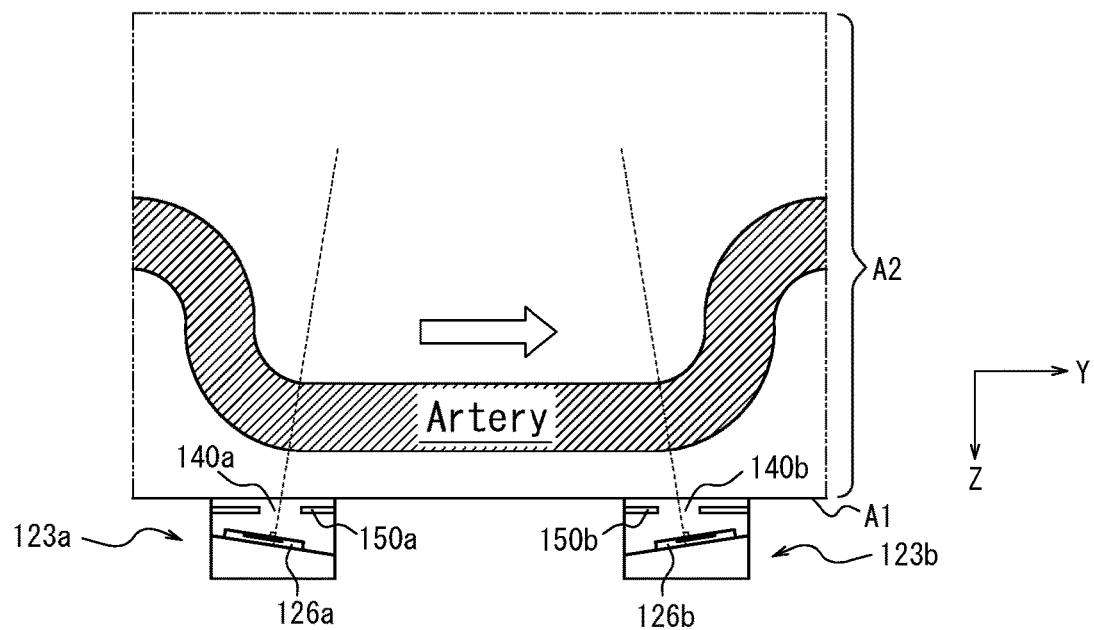
FIG. 11B is a schematic diagram illustrating the arrangement, on the test site, of the light receiving element and the light emitting elements of the measuring apparatus according to the fifth embodiment.

For the sake of easy understanding of the arrangement of the light receiving elements and the light emitting elements of the measuring apparatus 100 according to one embodiment with respect to the artery, FIG. 11A and FIG. 11B schematically illustrate the arrangement of the light receiving elements and the light emitting elements at the test site. In the artery the blood flows in the positive direction of the Y-axis, and thus the pulse wave is transmitted in the same direction. Note that FIG. 11A illustrates, by way of example, among the two light emitting units of the sensor units, the light emitting unit 121a and the light emitting unit 121b alone. Also, FIG. 11B, by way of example, illustrates the light receiving units 123a and 123b of the sensor units, omitting the two light emitting units of each sensor unit.

Referring to FIG. 11A, the light emitting elements 124a and 124b included in the light emitting units 121a and 121b are inclined to the respective opposing sensor units 120b and 120a, and thus the optical axes of the light therefrom are inclined to the respective opposing sensor units 120b and 120a. In this arrangement, the light emitted from the light emitting element 124a has the optical axis inclined to the sensor unit 120b and thus is unlikely to reach the curved portion of the artery on the upstream side of the sensor unit 120a. Similarly, the light emitted from the light emitting element 124b has the optical axis inclined to the sensor unit 120a and thus is unlikely to reach the curved portion of the artery on the downstream side of the sensor unit 120b. That is, the region in which the light entering the inner living body A2 is scattered may be limited, to some extent, to the linear portion of the artery, and therefore the information about the pulse wave from the curved portion of the artery which causes the reverse phenomenon of the phase difference is unlikely to be included. Accordingly, the measuring apparatus 100 may accurately measure the pulse wave.

Referring to FIG. 11B, the light receiving elements 126a and 126b included in the light receiving units 123a and 123b are inclined to the respective opposing sensor units 120b and 120a, and thus the optical axes of the light entering the light receiving elements are also inclined to the respective opposing other sensor units 120b and 120a. Because of this arrangement, the light scattered by the curved portion of the artery on the upstream side of the sensor unit 120a is almost entirely eliminated, and the remaining scattered light enters the light receiving element 126a. Similarly, the light scattered by the curved portion of the artery on the downstream side of the sensor unit 120b is almost entirely eliminated, and the remaining scattered light enters the light receiving element 126b. That is, the scattered light detected by the light receiving elements 126a and 126b may be limited, to some extent, to the light scattered by the linear portion of the artery, and therefore the information about the pulse wave from the curved portion of the artery which causes the reverse phenomenon of the phase difference is almost entirely eliminated. Therefore, the measuring apparatus 100 may accurately measure the pulse wave. Also, since the light receiving elements 126a and 126b are disposed closer to the light-shielding plates 150a and 150b, the light scattered from the curved portion of the artery on the upstream side of the sensor unit 120a and on the downstream side of the sensor unit and 120b is more reliably eliminated, and thus a light-shielding effect is further improved.

Sixth Embodiment

FIG. 12A is a schematic diagram illustrating an arrangement of the sensor unit 120a of the measuring apparatus 100 according to one embodiment. FIG. 12B is a cross-sectional view taken from A-A of FIG. 12A for schematically illustrating a state in which the light emitting elements 124a and 125a and the light receiving element 126a of the measuring apparatus 100 according to one embodiment are arranged on the skin A1 on the surface of the subject's wrist. FIG. 12A illustrates the sensor unit 120a alone, omitting the sensor unit 120b. In the artery, the blood flows from bottom to top (in the positive direction of the Y-axis), and thus the pulse wave is transmitted in the same direction. In a state in which the sensor unit 120a is positioned vertically to the artery (the X-axis direction), the light emitting element 121a, the light receiving element 123a, and the light emitting element 122a are arranged in the mentioned order in the positive direction of the X-axis intersecting with the artery. In FIG. 12B illustrating the cross-sectional view of the FIG. 12A, in the artery, the blood flows from a front side of the paper to a rear side (in the positive direction of the Y-axis), and thus the pulse wave is transmitted in the same direction.

According to one embodiment, in addition to the inclination of the light receiving elements and the light emitting elements to the respective opposing sensor units as described in the fifth embodiment, the light emitting elements are also inclined to the artery. In one embodiment also, similarly to the other embodiments, in the positive direction of the Y-axis viewed from the sensor unit 120a illustrated in FIG. 12A, the other sensor unit 120b is arranged having a predetermined distance therefrom. Accordingly, directions of the inclinations of the light receiving elements and the light emitting elements to the respective opposing sensor units are in the Y-axis direction of FIG. 12B. On the other hand, the direction of the inclination of the light emitting elements to the artery is the X-axis direction of FIG. 12B. That is, the optical axis of the light entering the light receiving element 126a inclines to the positive direction of the Y-axis alone, and the optical axes of the light emitted from the light emitting elements 124a and 125a incline to the positive direction of the Y-axis direction and, also, to the X-axis direction as illustrated in FIG. 12B. Since the light emitting units 121a and 122a are arranged symmetrically to each other across the artery in the X-axis direction, the optical axes of the light emitted from the light emitting elements 124a and 125a incline to opposite directions along the X-axis. That is, in FIG. 12B, by way of example, the optical axis of the light emitted from the light emitting element 124a inclines to the positive direction of the X-axis, while the optical axis of the light emitted from the light emitting element 125a inclines to the negative direction of the X-axis.

With the structure as described above, in one embodiment, a peak of spatial intensity distribution of the light emitted from the light emitting elements 124a and 125a transmitted in the inner living body A2 inclines to a direction of the artery. That is, almost entire light emitted from the light emitting elements 124a and 125a reaches the artery, and thus the intensity of the light scattered by the artery is increased. Thereby, the intensity of the scattered light entering the light receiving element 126a increases, and an SN ratio of a signal output from the light receiving element 126a is improved. According to one embodiment, in other words, in comparison with a state in which the optical axes of the light emitting elements are not inclined to the direction of the artery, the waveform of the pulse wave with relatively less noise with respect to signal intensity may be acquired.

Figure 13:
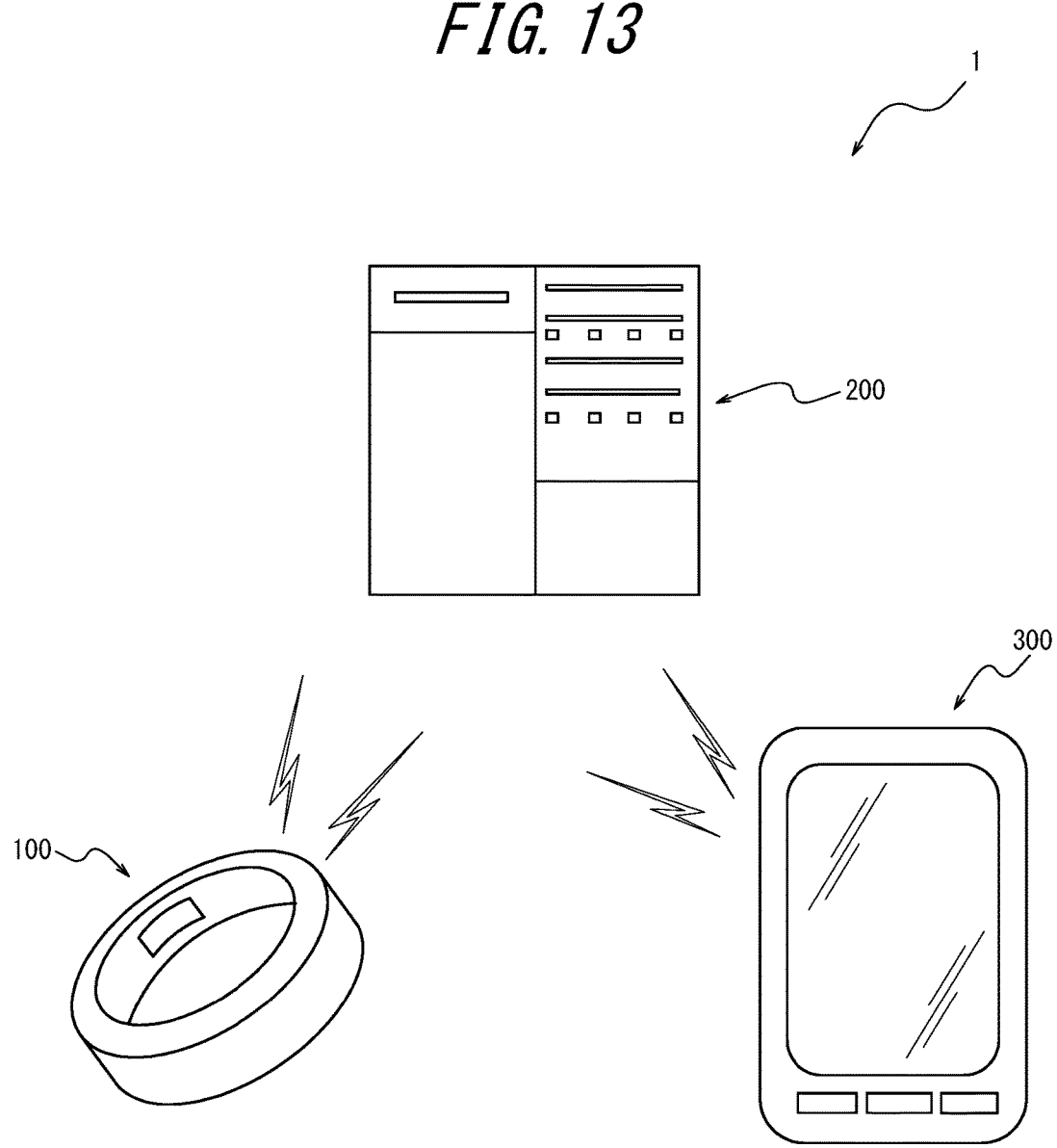
FIG. 13 is a schematic diagram illustrating a measuring system which includes the measuring apparatus.

FIG. 13 illustrates a schematic diagram of a measuring system 100 which includes the measuring apparatus 100 materializing at least one of the first to sixth embodiments described above. The measuring system 1 includes the measuring apparatus 100 and, also, a server 200 and a display unit 300. The server 200 aggregates the biological-information acquired by the measuring apparatus 100 and performs various information processing. The aggregation of the biological-information is performed by the measuring apparatus 100 of each subject transmitting data to the server 200 via a wired or wireless communication network. The display unit 300, based on the biological-information acquired by the measuring apparatus 100, displays a result of the information processing performed by the server 200. That is, the display unit 300 displays information based on the biological-information acquired by the measuring apparatus 100.

For example, the biological-information acquired by the measuring apparatus 100 is transmitted to the server 200 by a communication unit of the measuring apparatus 100. When the server 200 receives the biological-information transmitted from the measuring apparatus 100, a controller of the server 200, based on the biological-information of the subject received, performs various information processing. For example, the server 200 may store, in a storage unit of the server 200, the biological-information acquired by the measuring apparatus 100 as chronological data together with information about time at which the biological-information is acquired. The controller of the server 200, for example, by comparing the data stored with past data of the same subject already stored in the storage unit of the server 200 or data of another subject, generates optimal advice based on a result of the comparison. A communication unit of the server 200 transmits the chronological data of the subject acquired and the advice generated to the display unit 300. The display unit 300 displays the data and the advice received in a display. Or, the measuring apparatus 100 or the display unit 300 may have a function unit having functions similar to those of the storage unit and the controller of the server 200 and, in this case, the measuring system 1 may be configured without the server 200.

It is clear for those who are skilled in the art that the disclosure herein, without departing from the spirit or essential characteristics thereof, may be implemented in predetermined embodiments other than the embodiments described above. Accordingly, the foregoing descriptions are exemplary and not limiting. The scope of the disclosure herein is defined by the appended claims, rather than the foregoing description. Among all modifications, some modifications within a range of equivalents thereof are included therein. For example, functions and the like included in each means, constituent and the like may be rearranged without logical inconsistency, so as to combine a plurality of means or constituents together or to separate them.

The invention claimed is:

1. A measuring apparatus comprising:
a wearing portion to be worn by a subject; and a first sensor unit and a second sensor unit each supported by the wearing portion and each having two or more light emitting units and a light receiving unit, wherein the first sensor unit and the second sensor unit, in acquiring a biological-information of the subject when the wearing portion is worn by the subject, are arranged having a distance of 35 mm or less from each other along a predetermined blood vessel of the subject, and the light emitting units are arranged on both sides of the light receiving unit along a direction transverse to the predetermined blood vessel of the subject.

2. The measuring apparatus according to claim 1, wherein a light emitting element of the light emitting units of the first sensor unit and a light emitting element of the light emitting units of the second sensor unit are arranged having a distance of 35 mm or less from each other along the predetermined blood vessel of the subject.

3. The measuring apparatus according to claim 1, wherein a distance between the light emitting units of the first sensor unit and the light emitting units of the second sensor unit is shorter than a distance between the light receiving unit of the first sensor unit and the light receiving unit of the second sensor unit.

4. The measuring apparatus according to claim 1, wherein the light receiving unit includes an opening with a predetermined diameter.

5. The measuring apparatus according to claim 1, wherein the wearing portion is a belt to be worn by the subject on the wrist.

6. The measuring apparatus according to claim 1, wherein the biological-information is a pulse wave.

7. The measuring apparatus according to claim 6, comprising a controller for calculating a pulse wave velocity based on the pulse wave acquired.

8. A measuring system comprising:
the measuring apparatus according to claim 1; and
a display unit for displaying information based on the biological-information acquired by the measuring apparatus.

9. A measuring apparatus comprising:
a wearing portion to be worn by a subject; and
a first sensor unit and a second sensor unit each supported by the wearing portion and having a first light emitting unit and a light receiving unit, wherein the first sensor unit and the second sensor unit, in acquiring a biological-information of the subject when the wearing portion is worn by the subject, are arranged having a predetermined distance from each other along a predetermined blood vessel of the subject, and at least one of an optical axis of light emitted from the first light emitting unit of the first sensor unit and an optical axis of light entering the light receiving unit of the first sensor unit is inclined to the second sensor unit.

10. The measuring apparatus according to claim 9, wherein at least one of an optical axis of light emitted from the first light emitting unit of the second sensor unit and an optical axis of light entering the light receiving unit of the second sensor unit is inclined to the first sensor unit.

11. The measuring apparatus according to claim 9, wherein
the first light emitting unit includes a light emitting element,
the light receiving unit includes a light receiving element, and
at least one of the light emitting element and the light receiving element is arranged being inclined.

12. The measuring apparatus according to claim 9, wherein
the first light emitting unit includes a light emitting element,
the light receiving unit includes a light receiving element, and
at least one of direction of light emitted from the light emitting element and direction of light entering the light receiving element is changed.

13. The measuring apparatus according to claim 9, wherein a distance between the first light emitting unit of the first sensor unit and the first light emitting unit of the second sensor unit is shorter than a distance between the light receiving unit of the first sensor unit and the light receiving unit of the second sensor unit.

14. The measuring apparatus according to claim 9, wherein each of the the first sensor unit and the second sensor unit further include a second light emitting unit, and
in each of the first sensor unit and the second sensor unit, the first light emitting unit and the second light emitting unit are arranged on both sides of the light receiving unit along a direction transverse to the predetermined blood vessel of the subject.

15. The measuring apparatus according to claim 9, wherein the light receiving unit includes an opening with a predetermined diameter.

16. The measuring apparatus according to claim 9, wherein the wearing portion is a belt to be worn by the subject on the wrist.

17. The measuring apparatus according to claim 9, wherein the biological-information is a pulse wave.

18. The measuring apparatus according to claim 17, comprising a controller for calculating a pulse wave velocity based on the pulse wave acquired.

19. A measuring system comprising:
the measuring apparatus according to claim 9; and
a display unit for displaying information based on the biological-information acquired by the measuring apparatus.

* * * * *